United States Patent [19]

Shah et al.

[11]  4,143,174

[45]  Mar. 6, 1979

[54] FOOD COMPOSITION CONTAINING WHEY COLLOIDAL PRECIPITATE

[75] Inventors: Syed M. M. Shah; Anthony J. Luksas, both of Chicago, Ill.

[73] Assignee: Beatrice Foods Co., Chicago, Ill.

[21] Appl. No.: 598,873

[22] Filed: Jul. 24, 1975

[51] Int. Cl.² .................. A23C 21/00; A23D 5/00; A23L 1/04; A23L 2/00

[52] U.S. Cl. ............................ 426/570; 426/573; 426/583; 426/589; 426/599; 426/601; 426/602; 426/605; 426/620

[58] Field of Search ............ 426/583, 570, 573, 605, 426/654, 656, 657, 589, 599, 601, 602, 620; 260/112 R

[56] References Cited

U.S. PATENT DOCUMENTS

| | | | |
|---|---|---|---|
| 2,030,965 | 5/1935 | Clickner | 426/583 X |
| 2,349,969 | 5/1944 | Kremers | 426/583 |
| 2,495,706 | 1/1950 | DeVoss et al. | 426/573 |
| 2,555,514 | 6/1951 | Sharp et al. | 426/583 |
| 2,683,091 | 7/1954 | Singer et al. | 426/570 X |
| 2,780,548 | 2/1957 | Stamberg | 426/583 X |
| 3,620,757 | 12/1971 | Ellinger et al. | 426/570 X |
| 3,804,957 | 4/1974 | Purves | 426/605 |
| 3,842,062 | 10/1974 | Eastman | 426/583 X |
| 3,922,375 | 11/1975 | Dalan et al. | 426/583 |

Primary Examiner—Robert A. Yoncoskie
Attorney, Agent, or Firm—Murray & Whisenhunt

[57] ABSTRACT

A food-grade composition comprises a food of food-grade material, whey colloidal precipitate and water. The whey colloidal precipitate may effect the physical properties of clouding, stabilizing, gelling and emulsifying. The whey colloidal precipitate is a complex precipitate of whey in colloidal size ranges and is characterized by its ability to gel water and petroleum ether, is white in color, may be dried to a free-flowing powder and has no disagreeable whey taste.

26 Claims, No Drawings

FOOD COMPOSITION CONTAINING WHEY COLLOIDAL PRECIPITATE

The present invention relates to food compositions which have been modified in their properties by the inclusion of a whey colloidal precipitate. The modified properties may include stabilization, emulsification, thickening, clouding, gelling and viscosity control.

BACKGROUND OF THE INVENTION

Food compositions often require modification of their physical properties in order to provide desired textures (mouth-feel), viscosities or other physical properties. A wide variety of materials have been used in the art for this purpose, including various forms of starches, natural and synthetic gums, modified cellulosic derivatives, fractions from eggs, such as egg albumin, and fractions from vegetables, such as lecithin. Thus, compositions may be, for example, thickened with cornstarch, emulsified with lecithin, stabilized with carboxymethyl cellulose and the like. Generally, some of these modifiers will be more useful in certain applications than in others. For example, lecithin is an exceptionally good emulsifier for fat systems, but it has an inferior thickening ability. On the other hand, for example, starch has an exceptional ability for thickening, but it has an inferior emulsifying ability. Similarly some of the modifiers can be utilized simply by dissolving in an aqueous solution, e.g. some of the natural and synthetic gums, while others require a cooking step, such as the starches and egg derivatives, while others require both heating and cooling steps, such as gelatins.

As a result of the differences in efficiency for providing the properties as discussed above, it is necessary that careful selection of the modifier be made in order to obtain the required modification of physical properties in a relatively efficient and convenient manner. Thus, it is necessary to handle and use a wide variety of modifiers in the production of conventional kinds of prepared food compositions. Additionally, it may be necessary to include in any one food composition more than one of the modifiers, and thus increase not only the complexity of the production methods but the cost thereof. In this latter regard, the expense of certain of these modifiers can become appreciable when they must be used in higher concentrations to obtain the desired properties.

As can be appreciated from the foregoing, there is a need in the art for inexpensive modifiers which can function to provide a variety of modified physical properties in food-grade compositions and which can achieve the modified properties in convenient and efficient manners. Of course, modifiers of this nature must be non-toxic so as to constitute a food-grade modifier.

OBJECTS OF THE INVENTION

Accordingly, it is an object of the present invention to provide compositions wherein the physical properties have been modified by the inclusion of a particular non-toxic, food-grade modifier. It is a further object of the invention to provide such compositions where various modifications of the physical properties may be provided, including thickening, stabilization, emulsification, gelling, viscosity control and clouding, but with the same essential modifier. Other objects will be apparent from the following disclosure and claims.

BRIEF DESCRIPTION OF THE INVENTION

Briefly stated, the invention is based on the discovery that a particular whey colloidal precipitate efficiently functions as a food-grade composition modifier and that the whey colloidal precipitate can provide a wide variety of modified physical properties, depending upon the concentration of the modifier, the mode of its introduction into the composition, and the particular food-grade composition in which it is placed. The modifier may be used in any amounts desired in these compositions, since it is derived from a food (and hence is non-toxic and food-grade) and is quite bland in taste.

Thus, broadly stated, the present invention provides food-grade compositions which comprise a mixture of a food-grade material or a food (the latter in at least a flavor producing amount) and whey colloidal precipitate and water. At least a modifying amount of the whey colloidal precipitate is contained in the composition, especially up to 30% by weight of the water therein.

The resulting compositions may be a liquid of controlled viscosity or in a gelled state, including thixotropic gels. Alternately, the compositions may be an emulsion with the whey colloidal precipitant functioning as the primary emulsifier. The emulsion may be of a water-in-oil or oil-in-water type, or alternately, or in addition, include an air emulsion to provide a whipped and stabilized food material. The composition prepared by the present invention may be placed in a dried form for subsequent reconstitution by the addition of water. The present modifier can pass through a drying state without substantial degradation of its properties.

It is a further feature of the invention that the present modifier can function over a wide pH range scanning from acidic pHs through neutral to basic pHs, which constitutes a very advantageous property of the present modifiers.

The present modifier is obtained from whey which is a "food material," but is also considered, generally, a waste product. The methods of obtaining a modifier are quite simple and easy to operate, thus, resulting in a most inexpensive modifier. The modifier is also bland to the taste and, thus, may be used in the food composition in large amounts without significantly modifying the food taste.

DETAILED DESCRIPTION OF THE INVENTION

It is initially noted that the food-grade material or food of the present compositions may vary widely. Thus, the food may be of animal, dairy or vegetable origin and may be in a solid or liquid form. The food may be contained in the composition as a solution, suspension, gel, or solid (finely divided solid form of bulk solid form). The particular food and the particular form thereof are not critical to the invention and may be simply as desired.

The invention is applicable to any material which may be ingested by an animal, including humans. Thus, foodstuffs, pharmaceutical carriers, cosmetics (lipsticks, face creams, and bases), toothpaste and mouthwash are compositions which may be ingested and hence must be "food-grade." However, for simplicity sake, the following portions of the specification and claims will reference the foods or foodstuffs, but it is to be clearly understood that these terms are to embrace an ingested "food-grade" material.

The food contained in the composition must either have moisture associated therewith or water must be added to the food composition. In any event, the composition must have water present. The whey colloidal precipitate modifier of the invention can provide the wide variety of properties, discussed above, only in the presence of water. The amount of water is not critical so long as a "suspension," as defined hereinafter, is formed. Generally, the composition will contain at least 5%, e.g., at least 10% to 15% and up to 98% water, either as natural water in the food or added water.

The whey colloidal precipitate modifier may be obtained from a wide variety of whey, including vegetable whey and dairy whey. The whey may be derived, for example, from milk whey (e.g., cheese whey) or from a vegetable whey, such as soybean whey, cottonseed whey and the like. However, a very economical and convenient source of whey is cheese whey, and especially cottage cheese whey.

The present modifier is precipitated from the whey by various methods. Irrespective of the method, the precipitate obtained must be identifiable by reference to the following essential properties.

(A) The modifier, in pure form, is a non-proteinaceous, complex precipitate of whey. The modifier forms a colloidal suspension in amounts up to about 30% by weight of the water at room temperature, i.e., 68° F. In this context, however, it is important to understand that the suspension being referenced may have small amounts of solubilized components. The physical state is, however, more nearly a colloidal suspension. It has not been possible to determine if a true colloidal suspension exists in all applications. Nevertheless, up to about 30% by weight of the modifier may be "suspended" in water and produce a liquid which has the apparent properties of a colloidal suspension (with increasing concentrations, however, exceptional thickening of the "suspension" takes place — indicating the formation of a colloidal gel).

(B) The average particle size of the precipitate in a "suspension" may be in the range of less than 10μ and more usually less than 5μ. More often, the precipitate will have an average particle size of about 1μ or less, particularly in the range of about 1mμ to about 1μ. Of course, the processes for providing the precipitate can be operated in such a manner as to produce average particle sizes substantially less than the foregoing. The smaller particle sizes work equally well for the purposes of the invention and there is, essentially, no limit on the fineness of the particle size of the produced precipitate. Of course, as actually precipitated from the whey, the precipitate may be in agglomerated particle form and the average particle size in the agglomerated form may be far larger than in the "suspended" form.

(C) The precipitate will also be identifiable by virtue of its action on hydrocarbon liquid solvents. The present precipitate not only will gel aqueous solutions and suspensions, but will gel hydrocarbon solvents, such as petroleum ether. This is a distinguishing characteristic of the present precipitate and will serve as an easy means of distinguishing the present precipitate from other precipitates which might be obtained from whey but which do not qualify as the present whey colloidal precipitate.

(D) A further distinguishing characteristic of the present precipitate is the essentially white color and substantially bland taste thereof. The precipitate does not have the normal undesirable taste of whey. Thus, the present precipitate may be contained in an aqueous composition in any desired amount (up to about 30% by weight) and no substantial undesired flavor will be imparted to that composition.

(E) The precipitate, in essentially pure form, is non-proteinaceous. "In essentially pure form" means that the precipitate as finally used in a food composition will consist essentially of the non-proteinaceous complex and the amount of protein associated with the precipitate is sufficiently low that a water suspension of the precipitate will not yield a substantial protein precipitate when treated with trichloroacetic acid, i.e., a suspension having 5% by weight of trichloroacetic acid therein will not yield more than about 5% by weight of precipitated protein.

(F) Finally, the present precipitate is capable of being dried to an essentially free-flowing powder and therefore further distinguishes from other possible fractions of whey which are more usually hygroscopic in nature and cannot form dry, free-flowing powders.

Thus, for purposes of the present specification, the term "whey colloidal precipitate" is herein defined and used in the claims to mean a complex precipitate of vegetable or dairy whey which, in aqueous "suspension," is in the form of a colloidal suspension where the average particle size of the "suspension" is less than 10μ and amounts up to about 30% by weight thereof will cause gelation of water and petroleum ether, and wherein the precipitate is essentially white in color, exhibits no disagreeable taste in aqueous suspensions up to about 30% by weight thereof and can be dried to a free-flowing powder.

The present precipitate is obtained by causing a complex to form from the components in whey and causing the solubility of the complex to be exceeded such that precipitation thereof occurs. The precipitate must be substantially separated from the supernate (which contains the undesired lactose, etc.). Otherwise, the present properties will be either greatly reduced or be lost altogether. One method of causing precipitate is that of heating whey to a temperature of at least 80° C. Another method is treating whey with a water-soluble, non-toxic base to raise the pH of the whey sufficiently to cause precipitation or growing a yeast (e.g. baker's yeast) under aerobic conditions to raise the pH. The whey precipitate may be obtained by removing the other whey components, e.g. lactose, lactate, riboflavin, etc., which will leave the present complex in the whey liquid. If raw whey is used in the foregoing methods, the precipitate will contain substantial amounts of protein in addition to the present whey colloidal precipitate. The protein is not deleterious but does dilute the present precipitate. However, the term "whey colloidal precipitate" is to be construed in the present specification and claims as, in the embodiment of the invention, to be in the presence of substantial amounts of protein, e.g., there may be as much as equal amounts of the present precipitate and protein in the precipitate from whey.

In the preferred methods the whey is at least clarified whey, i.e., substantially free of casein fines, and more preferably the non-protein ultra-filtration fraction of whey. It is also preferable that the whey or fraction be concentrated to at least 10% total solids, e.g., from 15% to 32%, especially 23% to 28% total solids.

In the neutralization method, any food-grade base may be used, e.g., an alkali metal, alkaline earth metal and organic bases, such as lower alkane amines. The pH of precipitation will vary with the solids concentration, as well as the temperature of the whey, agitation, and the like. Generally speaking as the concentration of dissolved solids in the whey increases, the pH at which the precipitation occurs will decrease. Precipitation may occur at a pH as low as 5 for higher dissolved solid concentrations, but more often precipitation occurs at a pH of about 5.8 or higher. Even after precipitation commences, it is preferred to continue the raising of the pH in order to recover more of the whey colloidal precipitate. Precipitation will occur up to a pH of about 9, although at a pH of about 7.2, essentially all of the whey colloidal precipitate has been precipitated from the whey.

The supernate may be separated from the whey colloidal precipitate in any desired manner, but centrifugation is most convenient. At this time, the precipitate may be washed with water, either by simply spraying the precipitate during centrifugation or by re-suspending and re-centrifugation. Alternately, the precipitate may be dissolved in water at a low pH, e.g., at a pH of about 1.5 and again reprecipitating by raising the pH in the manner described above. However, since the precipitate is relatively pure with the first precipitation step, especially with clarified whey or whey fraction, further purification is not required.

Further, if desired, the final pH of the precipitate may be adjusted during the precipitation step by including therein a buffer system. For example, a diphosphate/monophosphate buffer system can be used.

It is not necessary to completely remove all of the supernate from the precipitate and the precipitate may be used in its wetted form. However, the solids of the wetted form should not contain more than 50% by weight of whey solids (on a dry basis). Usually, this will correspond to a required removal of at least 50% of the whey supernate, e.g., by decantation, centrifugation, etc.

Of course, if desired, the precipitate may be dried by any conventional means, such as a rotary dryer, oven dryer or spray dryer. The drying temperature and particular means of drying are not critical, but generally temperatures less than 180° F. are preferred since at above this temperature of the precipitate, some "browning" may occur.

While not required, it has been further found that even better results are obtained when the food composition (with the whey colloidal precipitate) also contains a nontoxic divalent cation. While the precipitate may be used in the presence of other materials and other ions, as desired, divalent cations appear to provide a further stabilization of the precipitate and thus enhance the properties achieved thereby. While any food-grade divalent cation may be used, calcium and phosphorous provide the best results and form the best mode of the invention. The calcium and phosphorous may be added to the precipitate by way of any desired food-grade compound, but simple bases and salts thereof are preferred. For example, the calcium may be added by way of calcium oxide, calcium hydroxide, calcium chloride, etc.

The precipitate may be incorporated into the food composition in any desired and conventional manner. For example, the precipitate may be simply dispersed in a suitable liquid, e.g., water, alcohol and mixtures thereof, and added to the foodstuff. Alternately, the foodstuff may be added to such a suspension or the precipitate may be added directly to the foodstuff. Usually, mixing will be required to provide adequate "suspension" of the precipitate in the mixture with the foodstuff. For example, a solution of natural flavors, artificial flavors and nutrients may be prepared to form an imitation orange juice. Such imitation orange juices, however, do not have the correct appearance, since they appear to be weak or diluted because of the transparency of the solution. By adding a small amount (e.g. 0.01% to 2% by weight) of the present precipitate to such solution, a clouding occurs and gives the appearance of a rich and undiluted orange juice. Thus, the precipitate may be used as a clouding agent.

As another example, precooked cereals are designed for re-suspension in hot water to provide a ready-to-eat cereal. The re-suspension and absorption in water, however, often does not give the correct appearance, i.e., an appearance of the conventionally cooked cereal. This is because the re-suspended cereal maintains a somewhat segregated condition from the water and gives a grainy and incompletely cooked appearance. Indeed, in extreme cases, the precooked cereal can slowly separate from the re-suspending water. The present precipitate is quite effective in avoiding such problems by stabilizing the re-suspended cereal in the water used for reconstitution thereof. This avoids a segregation and uncooked appearance and provides an improved mouth-feel of a thickened cereal, similar to conventionally cooked cereal. Thus, the present precipitate is effective as a stabilizer for stabilizing a suspended food solid in the aqueous composition.

Another example of such stabilization is where the present precipitate is added to a natural food, such as tomato juice, which contains an aqueous suspension of settlable solids. The present precipitate will substantially decrease the rate of settling of the solids of the tomato juice and keep the juice thick and rich appearing for longer periods of time.

The present precipitate may be also used to promote emulsification. For example, in conventional Italian and French-style salad dressings, the oil tends to rapidly separate from the water/vinegar emulsion. Conventional emulsifying agents have not been effective in preventing this separation for longer time periods. In one regard, this inability is due to the limits of the amount of conventional emulsifiers which may be used, consistent with not providing undesired side effects, such as poor taste. The present precipitate may be included in such salad dressings in large amounts, if desired, without adversely affecting the flavor, and provide an emulsion of the oil and vinegar components which is stable for a longer time period, e.g., an hour or longer. Thicker emulsions may also be prepared, such as mayonnaise, with the present precipitate and even emulsions containing air may be prepared. Thus, a conventional whipped topping comprises water, fat, protein and an emulsifier. A similar topping may be prepared with the present precipitate being substituted for either or both of the protein or the emulsifier and the whipped topping will be stable for long periods of time.

Also, the present precipitate may be used simply as a thickening agent. For example, a small amount of an artificial cheese flavor may be prepared in a water carrier and the flavor profile thereof may have the intensity of a cheese sauce prepared from natural cheese. However, the mouth feel and consistency thereof will not approximate a good cheese sauce. When sufficient conventional thickening agents, such as cornstarch and flour are incoporated into such compositions, the taste of the flour and cornstarch substantially depletes the taste of the artificial cheese flavor and an inordinate increase in the amount of the artificial cheese flavor is required or the diluted flavor will make the sauce less than totally acceptable. By using the present precipitate to thicken such flavored solutions or suspensions, the correct consistency and mouth feel may be achieved without sacrificing the level of flavor in the sauce. The degree of thickening may be as desired and can range from as low as that consistent with thin syrups (for example, a sugar solution thickened with the present precipitate to mimic a boiled syrup) to viscosities in the nature of emulsified desserts and sauces.

As noted above, the present precipitate has the distinct advantage of not only being a food-grade material, but it is, indeed, a fraction derived from a food and therefore, may be classified as a food. The present precipitate, therefore, can be incorporated into a food material in any desired amounts since it is a food and is, of course, non-toxic. Further, since it can be produced from a very inexpensive material by simple processes, the precipitate is quite inexpensive and may be used, economically, in large quantities.

The precipitate may be used from very low concentrations, such as those consistent with clouding or making a thin syrup, to higher concentrations, such as those consistent with a whipped topping or a stabilized mayonnaise. Generally speaking, based on the weight of the water in the food composition, the precipitate will be contained in the food composition in an amount from as little as 0.01% to as high as 30%, calculated as the essentially pure precipitate, but for most food compositions the amount will be from about 0.5%, e.g. 1-2% to above 15%, e.g. about 20% to 25%.

As noted above, the whey may be vegetable or dairy whey, either acid whey or sweet whey, as well as unclarified or clarified whey. In addition, the whey may be the permeate fraction of ultra-filtration of whey using semipermeable membranes, as is known in the art. A whey fraction similar to the permeate of ultra-filtration is de-proteinated whey (de-proteinated by conventional means such heating to 180° F. at a pH of below 5). Permeate and de-proteinated whey are defined as a whey fraction having essentially all of the protein removed therefrom so that 5% by weight of trichloroacetic acid in the whey will produce no more than 5% by weight of the precipitated protein. This latter material demonstrates that the present whey colloidal precipitate is derived from a portion of the whey which is essentially the non-protein portion and serves to emphasize that the present whey colloidal precipitate is not simply whey solids or precipitated whey protein.

The invention will be illustrated by the following examples, where all percentages in parts are by weight, but it is to be understood that the invention is not limited to these examples and extends to the breadth described above.

EXAMPLE I

PREPARATION OF THE PRECIPITATE

Two hundred pounds Beatreme acid whey were suspended into two hundred gallons of water and the suspension was heated to 102° F., with stirring, to dissolve the acid whey and disperse the non-soluble fractions in the water. The solution/dispersion was then passed to an ultra-filtration membrane (Westinghouse Membrane, D-150) and the permeate from the membrane was collected (essentially a protein-free fraction).

Fifty gallons of the permeate, at essentially room temperature, were stirred and potassium hydroxide was slowly added thereto to raise the pH of the permeate from about 4.4 to 5.6, at which pH a precipitate from the whey permeate began to form.

Similar procedures were carried out, except in the second procedure the pH was raised to 7.2; in the third procedure the permeate was heated to 180° F. and then the potassium hydroxide was added until a pH of 7.2 was reached; and in the fourth procedure, the permeate was heated to 180° F. and the pH was raised with potassium hydroxide to only 5.7.

In each of the procedures, substantial amounts of the precipitate were recovered from the whey, although the yield varied with the procedures. The precipitate from each procedure was dried. While laboratory analysis could demonstrate differences in the precipitate from the different procedures, the precipitate from each of the procedures functioned essentially the same in preparing food compositions. Accordingly, it is concluded that the precipitate may be recovered from the whey in the manners indicated above and the essential difference is in the yield of the recovery.

EXAMPLE II

PREPARATION OF THE PRECIPITATE

The first procedure of Example I was repeated except that the permeate was treated with calcium hydroxide. The precipitate recovered could not be distinguished from the precipitate of Example I, other than the presence of the calcium ion as opposed to the potassium ion. In testing the function of this precipitate, it was found to cloud a 10% solution of orange flavor crystals a level of precipitate of about 0.20% by weight of the water is required. A conventional whipped topping formulation was also stabilized with this precipitate, and it was found that it could be frozen and thawed without damage to the whipped topping and was stable at room temperature for one week. Also, a 10% solution of the precipitate was made in water. To about 100 parts of the solution were added about 200 parts of a liquid vegetable oil. When mixed, a stable oil-in-water emulsion was prepared and the oil remained suspended in the water without homogenization for about 5 hours.

EXAMPLE III

PREPARATION OF THE PRECIPITATE

Twenty-five hundred gallons of raw acid whey from cottage cheese were fed to a Westfalia separator operated at a bowl speed of 1600 rpms. The feed rate of the acid whey was 1600 gallons per hour. The sludge from the separator, containing casein fines and other insolubles, was discarded and the clarified supernate (the clarified acid whey) was recovered. The pH of the clarified acid whey was about 4.4. The total amount of clarified acid whey recovered was about 2450 gallons. To the recovered acid whey were added 45 lbs. of calcium hydroxide, in 5 lb. additions, until the pH stabilized at about 7.3. This, essentially, neutralized whey was then fed to the Westfalia separator with a bowl speed of 1600 rpms and at a feed rate of about 800 gallons per hour. About 315 gallons of wetted precipitate were recovered as the sediment from the separator. A portion of the wetted precipitate was resuspended in water at 50% by weight concentration and immediately spray-dried (1500 psi nozzle pressure, 290° F. inlet, 190° F. outlet) to an essentially white free-flowing powder. The remaining portion of the wetted precipitate was frozen for subsequent use.

EXAMPLE IV

This example illustrates the ability of the whey colloidal precipitate to emulsify oil and water to the extent that a thick mixture, similar to the viscosity of mayonnaise, may be prepared. A solution of the precipitate of Example III was prepared with 20 parts of the precipitate and 100 parts of water. To 100 parts of this solution were added 30 parts of 5% vinegar and the mixture was stirred. Fifty parts of sucrose were added thereto with stirring. Thereafter, 100 parts of liquid vegetable oil (soybean oil) were added and the mixture was homogenized. The emulsion which was prepared was stable and had the viscosity of a mayonnaise mixture.

EXAMPLE V

PREPARATION OF THE PRECIPITATE

Clarified acid cottage cheese whey (pH 4.0–4.5) was adjusted in pH to 3.5 with HCl (citric acid may also be used) to increase permeability of the whey colloidal forming components and to reduce membrane fouling. They whey was fractionated with a Westinghouse ultrafiltration membrane, D-150 (essentially protein-free).

The permeate was adjusted to a pH of 8.0 with KOH (NaOH may be used) to cause precipitation. After heating to 90° C. for 15 minutes, the solution was cooled and separated by centrifugation, resuspended in water and then spray dried as above to give a white, free-flowing powder.

EXAMPLE VI

The following ingredients were dry-blended:

| Ingredient | Parts by Weight |
| --- | --- |
| Sucrose | 873 |
| Citric acid | 47.5 |
| FDA Yellow coloring | 23 |
| Sodium citrate | 10 |
| Ascorbic acid | 2.5 |
| Oil-soluble orange flavor | 3.5 |
| Spray-dried orange flavor | 2.0 |

The dry-blended ingredients were mixed with the whey colloidal precipitate prepared by the method of Example I in a weight ratio of precipitate to blend of 1:26 (3.8%).

This mixture was then mixed with chilled water (40° F.) in a weight ratio of water to mixture of 1:7.6 to provide an orange flavor drink having the clouded appearance of orange juice.

EXAMPLE VII

The following ingredients were melt blended at 140° F.:

| Ingredients | Parts by Weight |
| --- | --- |
| 100° F melt soy oil | 1826 |
| 152° – 158° F hydrogenated soy oil | 67 |
| mono- and di-glycerides of vegetable oils | 443 |
| glycerol lacto esters of fatty acids, M.P. 115° – 130° F | 118 |
| glycerol lacto esters of fatty acids, M.P. 97° – 103° F | 96 |

In a separate container were dispersed the following ingredients:

| Ingredients | Parts by Weight |
| --- | --- |
| Water | 5000 |
| Sodium caseinate | 148 |
| Corn syrup solids D.E. = 24 | 1042 |
| Corn syrup solids D.E. = 42 | 1032 |
| K$_2$HPO$_4$ | 112 |
| Whey Ppt. of Example I | 158 |

The dispersion was pasteurized at 160° F. for 30 minutes and at this temperature were added the melt-blended ingredients and again brought to 160° F. for 30 minutes. The mixture was cooled to 120° F. and homogenized at 1500 psi. The homogenized mixture was spray dried in a box drier (67/20 nozzle at 1500 psi pressure; 290° F. inlet, 190° F. outlet) to a free-flowing powder. The powder was tempered for six days.

Three parts of the powder, one part of sucrose and with 8 parts of chilled whole milk (40° F.) were mixed in a beater/blender at low speeds for 30 seconds and then whipped at high speeds for 5 minutes to provide a whipped topping (a procedure known to the art).

EXAMPLE VIII

A melt-blend was prepared by heating 1980 parts of 100° F. melt hydrogenated soy oil and 110 parts of 142°–148° F. melt hydrogenated vegetable oil. In a separate container were dispersed 13,000 parts of warm water (120° F.), 1480 parts of cane sugar, 2350 parts of modified starch (Capsul-National Starch), 3990 parts of partially hydrolysed starch and 200 parts of the whey colloidal precipitate of Example I.

The dispersion and melt-blend were pasteurized (160° F., 30 min.) and homogenized (600 psi, 1st stage, 2600 psi, 2nd stage), cooled to 120° F. and spray dried in a box drier (67/20 nozzle at 1500 psi, 290° F. inlet, 190° F. outlet) to a free flowing powder. Acceptable clouding of orange and grape drinks could be provided by adding from 0.02% to 2.00% of the powder to the drink (weight/volume).

EXAMPLE IX

PREPARATION OF THE PRECIPITATE BY LACTOSE CRYSTALIZATION

Clarified cottage cheese whey was past through an ultra-filtration membrane (Abcor-Ultra-Filtration Membrane for Cheese Whey) and the permeate was adjusted to a 35% solution (weight/volume). This solution is heated to insure complete solution (130° F. for 5 minutes), cooled to 40° F. and and maintained at this temperature with mild stirring. Lactose began to precipitate and the precipitation was continued for about 20 hours. The slurry was centrifuged at low RPMs to remove the lactose crystals. Thereafter a high RPM centrifugation was used to cause the whey colloidal precipitate to be removed from the delactosed solution.

EXAMPLE X

PREPARATION OF THE PRECIPITATE BY TEMPERATURE

The permeate of Example IX was adjusted to a 6.5% solution and autoclaved at 250° F. for 15 minutes. The precipitate is removed by decanting or filtration or centrifugation.

Thus, the invention provides compositions where the physical properties are modified to cause clouding, stabilization, emulsification, thickening and gelling. The amount of the present precipitate required for providing these functions, generally, increases in the foregoing named order of the functions. For example, in some systems, 0.1% of the precipitate, based on the water, will cause clouding, while full stabilization may be 1.0%, stable emulsion may require 3%, thickening may require 10% and gelling may require 18%. All of this, however, is, obviously, easily determined by a simple test for any particular food composition.

It is also apparent that the present whey colloidal precipitate may be used to provide combinations of the foregoing properties and can thus be used in very special applications.

For example, the precipitate may be used to not only thicken a non-dairy "milk shake," but will stabilize the mixture to reduce the formation of ice crystals, cloud the mixture and emulsify with air when whipped.

Accordingly, the invention extends to the spirit and scope of the annexed claims.

What is claimed is:

1. A food composition comprising a food and from 0.01% to 25% of a modifier consisting essentially of a non-proteinaceous colloidal precipitate of whey, and water, said whey colloidal precipitate being the product of a process having at least one step (a) raising the pH of whey to at least 5.8, and (b) heating the whey to a temperature of at least 80° C. for a time sufficient to produce said precipitate, and the precipitate of said process being identifiable as a complex precipitate which in aqueous suspension has an average particle size of less than 10 microns, is essentially white in color, exhibits no disagreeable taste in aqueous suspensions of up to about 30%, can be dried to a free-flowing powder, is capable of gelling water and petroleum ether, said whey being priorly sufficiently de-proteinated so that 5% by weight of trichloroacetic acid therein will not yield more than 5% by weight of precipitate protein.

2. The composition of claim 1 wherein said food composition is an aqueous liquid, emulsion, aqueous suspension, or aqeueous gel.

3. The composition of claim 1, wherein said composition is an aqueous suspension and said composition contains a suspension stabilizing amount of the whey colloidal precipitate.

4. The composition of claim 1 wherein said food composition is an emulsion and the composition contains an emulsifying amount of the whey colloidal precipitate.

5. The composition of claim 1 wherein said food composition is an aqueous gel and the composition contains a gelling amount of the whey colloidal precipitate.

6. The composition of claim 4 wherein the emulsion contains an oil or fat.

7. The composition of claim 6 wherein said food composition is an imitation mayonnaise, a whipped topping or salad dressing.

8. The composition of claim 7 wherein said food composition is an emulsified salad dressing.

9. The composition of claim 1 wherein said food composition is an aqueous clouded suspension or an aqueous solution.

10. The composition of claim 9 wherein the solution or suspension contains a fruit flavor.

11. The composition of claim 1 wherein the whey colloidal precipitate is substantially neutralized.

12. The composition of claim 1 in a dried form.

13. The composition of claim 1 wherein the pH of the precipitate is between 5.0 and 8.5.

14. The composition of claim 13 wherein the pH is between 6.5 and 7.8.

15. The composition of claim 1 wherein said food composition is imitation orange juice.

16. The composition of claim 1 wherein said food composition is precooked cereal.

17. The composition of claim 1 wherein said food composition is tomato juice.

18. The composition of claim 1 wherein said food composition is mayonnaise.

19. The composition of claim 1 wherein said food composition is artificial cheese sauce.

20. The composition of claim 1 wherein the amount of modifier is between b 0.5% and 25%.

21. The composition of claim 1 wherein the amount of modifier is between 1% and 25%.

22. The composition of claim 1 wherein the amount of modifier is between 15% and 25%.

23. The composition of claim 1 wherein the whey colloidal precipitate is derived from clarified whey.

24. The composition of claim 1 wherein the whey colloidal precipitate is derived from ultrafiltered whey permeate.

25. The composition of claim 1 wherein the food composition also contains a non-toxic divalent cation selected from calcium and phosphorous in amounts wherein the properties of the whey colloidal precipitate for stabilization of aqueous suspensions are enhanced.

26. The composition of claim 1 wherein said food composition is a whipped topping.

* * * * *